United States Patent
Li et al.

(10) Patent No.: US 11,871,895 B2
(45) Date of Patent: Jan. 16, 2024

(54) RAMAN SPECTROSCOPY REPORTERS AND METHODS FOR MOLECULAR IMAGING OF TISSUE IN VIVO

(71) Applicant: THE JOHNS HOPKINS UNIVERSITY, Baltimore, MD (US)

(72) Inventors: Ming Li, Baltimore, MD (US); Ishan Barman, Baltimore, MD (US); Martin Pomper, Baltimore, MD (US); Sangeeta Ray, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 417 days.

(21) Appl. No.: 15/778,236

(22) PCT Filed: Nov. 23, 2016

(86) PCT No.: PCT/US2016/063455
§ 371 (c)(1),
(2) Date: May 23, 2018

(87) PCT Pub. No.: WO2017/091640
PCT Pub. Date: Jun. 1, 2017

(65) Prior Publication Data
US 2018/0344164 A1    Dec. 6, 2018

Related U.S. Application Data

(60) Provisional application No. 62/259,131, filed on Nov. 24, 2015.

(51) Int. Cl.
| | |
|---|---|
| *A61B 5/00* | (2006.01) |
| *G01N 33/574* | (2006.01) |
| *A61K 49/00* | (2006.01) |
| *A61B 1/06* | (2006.01) |
| *G01N 21/65* | (2006.01) |
| *G01N 33/543* | (2006.01) |
| *B82Y 15/00* | (2011.01) |

(52) U.S. Cl.
CPC ............ *A61B 5/0071* (2013.01); *A61B 1/063* (2013.01); *A61B 5/0084* (2013.01); *A61B 5/4381* (2013.01); *A61K 49/00* (2013.01); *G01N 21/658* (2013.01); *G01N 33/54346* (2013.01); *G01N 33/574* (2013.01); *G01N 33/57434* (2013.01); *B82Y 15/00* (2013.01)

(58) Field of Classification Search
CPC ............ C12Q 2563/155; C12Q 1/6816; C12Q 1/6825; C12Q 1/6886; C12Q 2565/632; A61K 41/0052; A61K 49/0093; A61K 41/0057; A61K 47/60; A61K 49/1821; A61K 51/1244; A61K 49/00; A61K 49/0002; A61K 49/1824; A61K 33/24; A61K 39/39558; A61K 47/02; A61K 47/6929; A61K 51/025; A61K 9/51; A61K 9/5115; A61K 2123/00; A61K 2121/00; A61P 35/00; A61B 18/04; A61B 18/1815; A61B 18/20; A61B 10/0041; A61B 1/00013; A61B 5/0075; A61B 2018/00547; A61B 5/4381; A61B 5/0071; A61B 1/063; A61B 5/0084; A61N 5/062; A61N 5/00; A61N 5/0603; G01N 33/54346; G01N 21/658; G01N 33/587; G01N 33/574; G01N 33/57434; C01P 2002/52; C01P 2004/80; B82Y 15/00
USPC ........ 424/1.11, 1.65, 1.81, 9.1, 9.2, 9.3, 9.4, 424/9.5, 9.6
See application file for complete search history.

(56) References Cited

U.S. PATENT DOCUMENTS

| | | | |
|---|---|---|---|
| 8,795,628 B2 | 8/2014 | Gambhir et al. | |
| 9,987,358 B2* | 6/2018 | Vo-Dinh | G01N 33/582 |
| 2008/0241828 A1 | 10/2008 | Wu et al. | |
| 2011/0230760 A1* | 9/2011 | Gambhir | G01N 21/658 |
| | | | 600/431 |
| 2011/0275061 A1 | 11/2011 | Weidemaier et al. | |

FOREIGN PATENT DOCUMENTS

| | | |
|---|---|---|
| EP | 2461163 A2 | 6/2012 |
| WO | 2006066965 A3 | 6/2006 |
| WO | 2008122035 A1 | 10/2008 |
| WO | 2012135592 A3 | 10/2012 |

OTHER PUBLICATIONS

Banerjee et al, Journal of Medicinal Chemistry, pp. 2657-2669 (Year: 2014).*
Vallabhajosula et al, Clin. Cancer Res., vol. 11, Supplement 19, pp. 7195s-7200s (Year: 2005).*
Liu et al, Frontiers in Chemistry, Aug. 2015, vol. 3, Article 51, pp. 1-7 (Year: 2015).*
Schutz et al, Chem. Commun., vol. 47, pp. 4216-4218 (Year: 2011).*
Hillier et al, Cancer Research, vol. 69, No. 17, pp. 6932-6940 (Year: 2009).*
Banerjee, S., et al., "Sequential SPECT and Optical Imaging of Experimental Models of Prostate Cancer with a Dual Modality Inhibitor of the Prostate-Specific Membrane Antigen" Angew. Chem. Int. Ed. (2011) vol. 50, No. 39, pp. 9167-9170.
Banerjee et al., Sequential SPECT and Optical Imaging of Experimental Models of Prostate Cancer with Dual Modality Inhibitor of the Prostate-specific Membrane Antigen. Angew. Chem. Int. Ed. 2011, 50:9167-70.

(Continued)

*Primary Examiner* — D. L. Jones
(74) *Attorney, Agent, or Firm* — Casimir Jones, SC; Jeffrey W. Childers (57) ABSTRACT

The present invention provides a targeted nanoplex platform for in vivo imaging and theranostic imaging of cancer to simultaneously provide non-invasive assessment of tumor burden and cancer-selective treatments.

21 Claims, 4 Drawing Sheets

(56) References Cited

OTHER PUBLICATIONS

Chen et al., Radiohalogenated prostate-specific membrane antigen (PSMA)-based ureas as imaging agents for prostate cancer. J Med Chem 2008, 51:7933-43.

Li et al., 2015 Multiplexed detection of serological cancer markers with plasmon-enhanced Raman spectro-immunoassay., Chem Sci 2015, 6:3906-14.

Li et al., Shedding Light on the Extinction-Enhancement Duality in Gold Nanostar-Enhanced Raman Spectroscopy., Angew Chem Int. Ed. 2014, 53:14115-9.

Perkins et al., Conventional and Immunoelectron Microscopy of Mitochondria (Eds.: Leister, D. and Hermann J. M.) Humana Press, 2007, 467-483.

Liu et al., Constitutive and Antibody-induced Internalization of Prostate-specific Membrane Antigen. Cancer Res. 1998, 58:4055-60.

Chandran et al., Characterization of a targeted nanoparticle functionalized with a urea-based inhibitor of prostate-specific membrane antigen (PSMA) Cancer Biol. Ther. 2008, 7, 974-982.

Chen et al., PSMA-Targeted Theranostic Nanoplex for Prostate Cancer Therapy., ACS Nano 2012, 6, 7752-7762.

Weineisen et al., 68Ga-and 177Lu-labeled PSMA i and T: Optimization of a PSMA-targeted theranostic concept and first proof-of-concept human studies, 2015 J Nucl Med 56:1169-76.

Benesova et al., Preclinical evaluation of a tailor-made DOTA-conjugated PSMA inhibitor with optimized linker moiety for imaging and endoradiotherapy of prostate cancer, 2015 J Nucl Med 56:914-20.

Ferro-Flores et al., Theranostic radiopharmaceuticals based on gold nanoparticles labeled with 177Lu and conjugated to peptides, 2015 Current Radiopharmaceuticals 8(2):150-9.

Del Mistro et al., Surface-enhanced Raman spectroscopy of urine for prostate cancer detection: a preliminary study, 2015 Analytical and Bioanalytical Chemistry 407:3271-75.

Meneghetti et al., Plasmonic nanostructures for SERRS multiplexed identification of tumorassociated antigens., 2012 Small 8(24):3733-3728.

\* cited by examiner

RAMAN SPECTROSCOPY REPORTERS AND METHODS FOR MOLECULAR IMAGING OF TISSUE IN VIVO

CROSS-REFERENCE TO RELATED APPLICATIONS

This application is a 35 U.S.C. § 371 U.S. national entry of International Application PCT/US2016/063455 having an international filing date of Nov. 23, 2016, which claims the benefit of U.S. Provisional Application No. 62/259,131, filed Nov. 24, 2015, the content of each of the aforementioned applications is herein incorporated by reference in their entirety.

BACKGROUND OF THE INVENTION

The past decade has witnessed enormous research efforts undertaken in the development of biomedical platforms for rapid screening, simultaneous diagnostics and treatment, and targeted therapy of prostate cancer with a minimal invasion manner to achieve personalized medicine. For the prostate cancer care and management, the most ideal strategy would directly eliminate cancer cells without damaging normal cells or tissues. Despite intensive efforts, prostate cancer is still the most prevalent non-cutaneous malignancy in American males and the second cause of cancer death in men, behind only lung cancer. The American Cancer Society estimates that about 220,800 new cases will be diagnosed with prostate cancer in 2015, accounting for approximately 14% of all new cancer cases in American men, and about 27,540 deaths will be caused by prostate cancer in 2015. One of reasons that account for this mortality is the inability to predict which patients have indolent as opposed to aggressive disease, complicating the choice of appropriate therapy; and another reason is the difficulty in assuring a clear surgical margin during prostatectomy. In clinic, structural imaging modalities such as computed tomography (CT), magnetic resonance imaging (MRI) and ultrasound are being employed to identify anatomical patterns and to provide basic information regarding tumor location, size, and spread based on endogenous contrast. However, these imaging modalities are inefficient in detecting tumors and metastases that are smaller than 0.5 cm and they can barely distinguish between benign and cancerous tumors. There is a pressing demand for a reliable, sensitive imaging tool for prostate cancer screening and diagnostics.

Molecular imaging that integrates molecular biology with in vivo imaging has been widely employed to gain information regarding biological processes and to identify diseases based on the molecular biomarkers characteristic of the disease progression. Currently, positron emission tomography (PET) and single photon emission computed tomography (SPECT) are the main molecular imaging modalities in clinical use, however, they are nonspecific and fail to distinguish at cellular and molecular levels. Targeted molecular imaging via sensing of biomarkers characteristic of prostate cancer progression offers multiple advantages toward achieving the goal of effective cancer-selective treatments without systemic toxicity. Prostate-specific membrane antigen (PSMA) is a type II integral membrane protein that is significantly over-expressed on the cell surface of nearly all prostate cancers, particularly in androgen-independent, advanced and metastatic diseases. Thereby, PSMA has become an established biomarker for the progression of prostate cancer and has attracted significant attention as a target for the delivery of imaging and therapeutic agents.

The ability to selectively detect PSMA over-expression in prostate cancer offers the promise for new avenues of diagnosis and earlier therapeutic intervention for patients at risk of an aggressive metastatic stage of the diseases. Previous studies showed that SPECT, MM and fluorescence imaging modalities enable the visualization and delineation of tumor margins precisely during and following resection through targeting to the PSMA using a low molecular weight, urea-based PSMA-targeting moiety. However, sensitivity still remains a limiting factor in both SPECT and MRI. In addition, despite the high sensitivity and spatial resolution of fluorescence imaging, live-cell fluorescence imaging usually suffers from the photobleaching and phototoxicity. A commercial need exists to create live cell and tissue imaging methods that may be used in vitro and in vivo with high resolution to accurately diagnose, treat, and monitor the progression of disease such as cancers in humans.

SUMMARY OF THE INVENTION

One embodiment of the present invention relates to a method of molecular imaging of biological material using Raman spectroscopy reporters comprising the steps of: 1) providing a nanoplex comprising a SERS tag and a targeting agent that binds to a biological material; 2) applying the nanoplex to the biological material so that the nanoplex binds to the biological material; 3) energizing the nanoplex with an energy source to create a Raman signal; 4) detecting the Raman signal; and 5) determining the image. The methods of the present invention may be used to image in vivo, or in vitro, biological material. Biological material may comprise a cell, cells, tissue(s), and/or organ(s). Preferably, the biological material is cells, tissues and/or organs that are affected by a disease such as cancer. The targeting agent used in the present invention is a substance that binds specifically, and preferably with high affinity, to cancer cell(s), tissue(s), and/or organ(s). Such targeting agents include PSMA binding agents such as a NETS-ester-urea-based small molecule inhibitor of PSMA wherein a nanoplex of the present invention binds to tissue or cells inflicted with prostate cancer. The nanoplex is activated by an energy source, preferably an endoscopic laser during in vivo applications, which emits light in the range of 700 nm to 1000 nm. The nanoplex emits a Raman signal that is detected by a light detector connected to a computer with an attached screen that displays the image.

Another embodiment of the present invention is a method of molecular imaging of a therapeutic agent by providing a nanoplex comprising a SERS tag, a targeting agent that binds to biological material, and a therapeutic agent. The nanoplex is applied and binds to the biological material and is energized by an energy source to create a Raman signal that is detected by a light detector. The location of the therapeutic agent on the biological material is displayed on a screen attached to a computer that is connected to the light detector.

Another embodiment of the present invention is a Raman spectroscopy nanoplex for molecular imaging of biological material comprising a nanoplex that comprises a SERS tag, a targeting agent, and a therapeutic agent. The targeting agent is a substance that preferably binds to one or more cancer, wherein the therapeutic agent enhances cancer cell death. The Raman spectroscopy nanoplex may be applied to in vivo, or in vitro, biological material to form images of therapeutic agent localization associated with biological material on a computer screen as further described in the specification.

DETAILED DESCRIPTION OF THE INVENTION

Surface-Enhanced Spectroscopy

Surface-enhanced Raman spectroscopy (SERS) has recently emerged as a powerful analytical tool for chemical analysis and biological sensing through providing ultrahigh sensitivity and intrinsic chemical fingerprint information. The significant signal enhancement arises from the proximity of the Raman molecule to the intense localized plasmonic fields created by the nanostructured metals. SERS exhibits significant advantages over fluorescence methods including molecular specificity, less interference from biological matrices, resistance to photobleaching and phototoxicity, and powerful multiplexing capability due to narrow spectral bands. As part of the present invention SERS is determined to be particularly suitable for biomedical applications including sensitive in vivo imaging of cells and tissues.

The present invention has overcome the challenges and limitations of live-cell imaging in conventional modalities, by the development of a SERS-based imaging platform for the live-cell and tissue imaging both in vitro and in vivo by developing high specificity, high sensitivity and photostability in SERS. Several important features exist in the present SERS bioimaging process.

Formation of SERS Tags

SERS tags are generally defined as comprising one or more Raman reporter molecules, a high SERS-active gold nanostar (GNS) and a thin protective layer wherein the thin protective layer is preferably silica. It is preferred that a Raman reporter molecule is located between the GNS and the thin protective layer. Raman reporter molecules suitable for the present invention include 4-nitrothiophenol (NTP), 4-mercaptobenzoic acid (MBA), malachite green isothiocyanate (MGITC), rhodamine B isothiocyanate (RBITC), and combinations thereof. Suitable materials for the thin protective layer include $SiO_2$, polyethylene glycol (PEG), poly(allylamine hydrochloride) (PAH), poly-(acrylic acid) (PAA) or combinations thereof. A SERS tag may further comprise MPEG-silane and/or a cross linker, preferably attached to the thin protective layer. A cross linker may be used for attaching a targeting agent or therapeutic agent to a SERS Tag.

In some embodiments the sandwich SERS tag is preferably employed, in which a Raman reporter layer, 4-nitrothiophenol (NTP), is sandwiched between the GNS and the thin silica protective layer, and is used in the present invention. The developed SERS tag exhibits fantastic brightness due to the high SERS activity of GNS and encapsulation of a large number of NTP, benefiting both in vitro and in vivo imaging of high sensitivity and spatial resolution. Unlike conventional fluorescence method, less photobleaching occurs under the SERS imaging conditions of the present invention. The SERS tags of the present invention preferably include a silica protection layer that also prevents the leakage of NTP molecules into the surrounding medium and further improves the long-term stability.

Figure 1A:
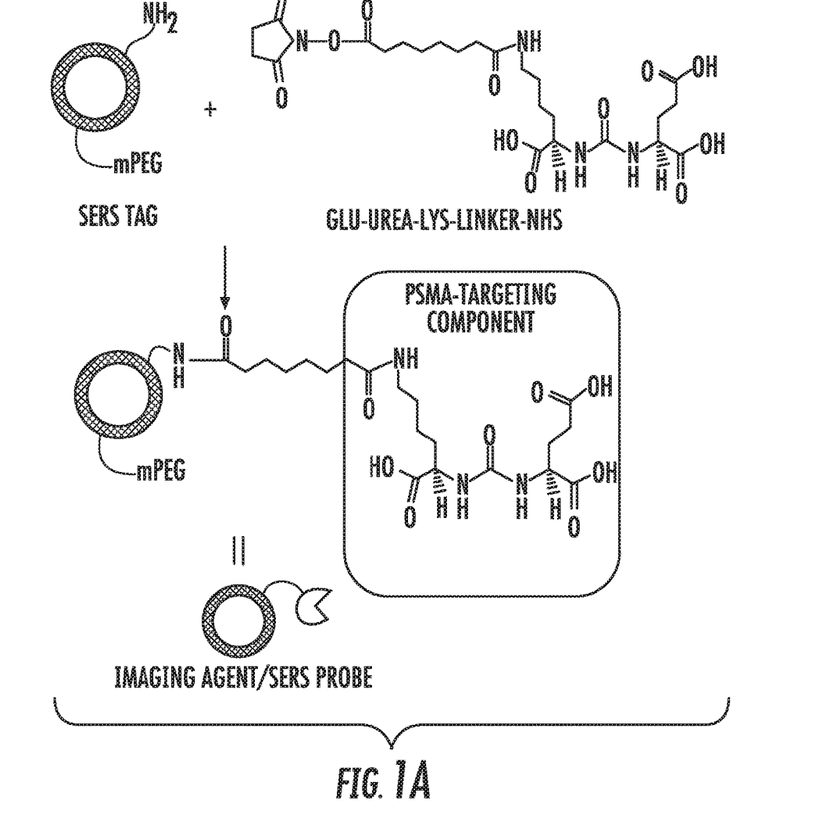
FIG. 1A-1C illustrates a synthesis of a nanoplex. (A) Schematic illustration of nanoplex conjugated with urea-based PSMA targeting component. Glu-urea-Lys-linker-NHS was conjugated onto the SERS tag surface through the amine coupling chemistry to prepare the nanoplex. The SERS tag was prepared through sandwiching a large number of Raman reporter molecules, 4-nitrothiophenol, between the highly SERS-active gold nanostar and the thin silica protective layer. (B) TEM image of the sandwich SERS tag encoded with 4-nitrothiophenol. (C) SERS spectra of i) sandwich SERS tag and ii) nanoplex; both of them show similar SERS signatures characteristic of the Raman reporter molecule. SERS spectra were recorded with a laser source of 785 nm excitation wavelength (5 mW power, 1 s integration time).
Figure 1B:
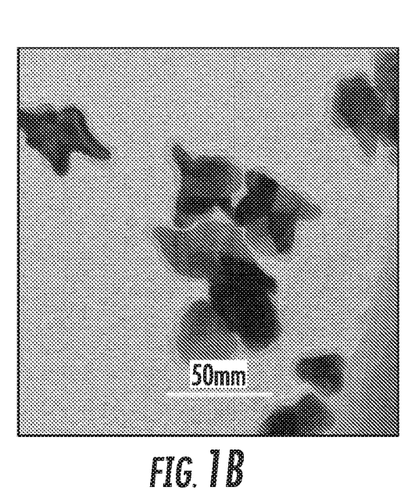
Figure 1C:
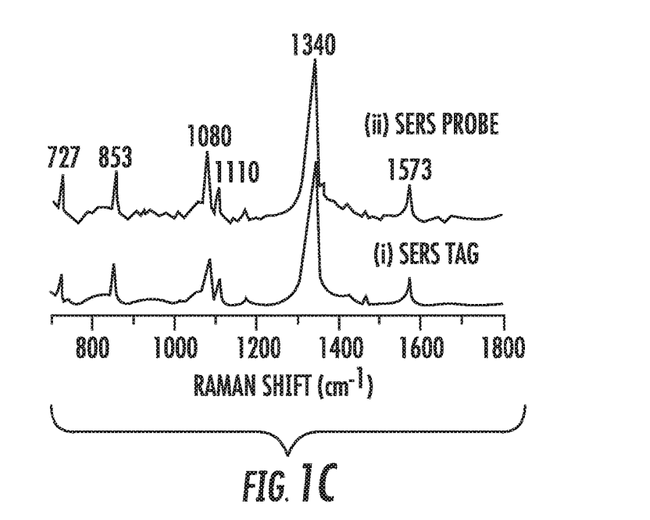
Figure 2A:
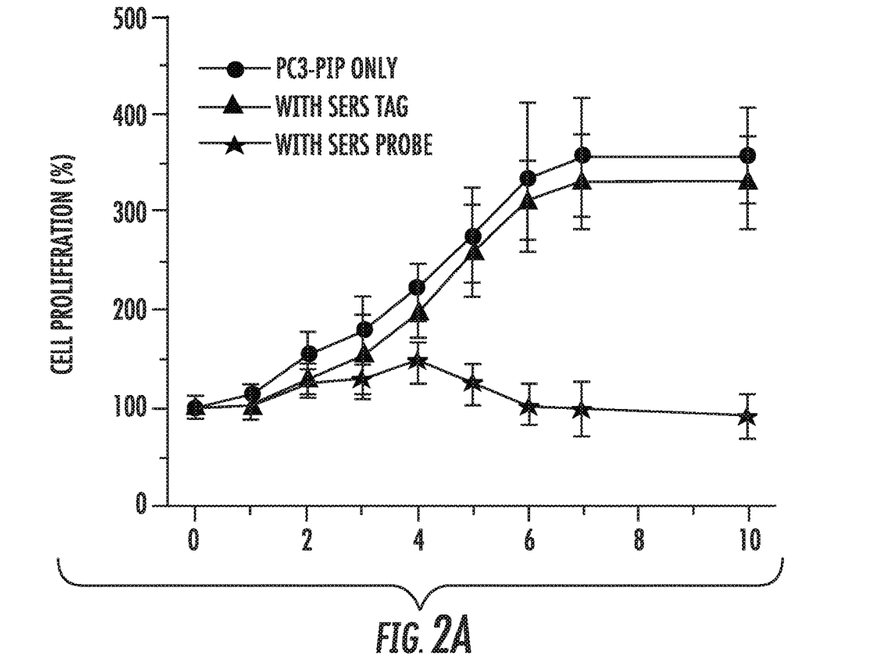
FIG. 2A-2B illustrates in vitro cellular cytotoxicity test of a nanoplex. (A) Cell growth of PSMA+PC3-PIP cells in the absence or presence of SERS tag and nanoplex. The cells were seeded onto the 96-well plate containing RPMI 1640 with 10% FBS and 1% Penicillin-Streptomycin at a 37° C./5% $CO_2$ incubator. The concentration of both SERS tag and nanoplex is 50 pM in their respective cases. The cell growth was measured by a WST-1 assay. (B) Change of cell number of PC3-PIP, PC3-Flu and breast cancer MDA-MB-231 cells in the absence or presence of SERS tag and nanoplex after incubation for 7 days in incubation medium.
Figure 2B:
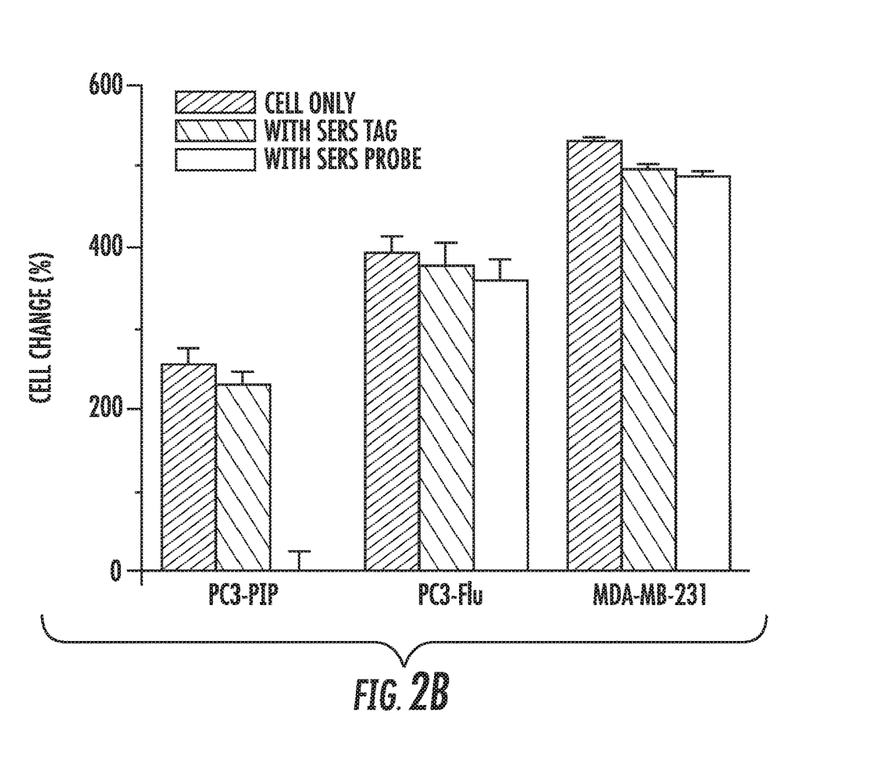

SERS tags are prepared by sandwiching Raman reporter molecules between the highly SERS-active GNS and the thin silica protective layer. To maximize SERS enhancement, a GNS with a localized surface plasmon resonance (LSRP) absorbance maximum of 750 nm as the SERS substrate in the synthesis of SERS tag was used (FIG. 1). The chemical binding of NTP onto the GNS surface through the strong—S—Au interaction leads to a single layer of NTP for SERS Tag, and the following silica protective layer prevents the leakage of NTP into the surrounding medium and thereby stabilizes the SERS signal (FIG. 2). The synthesized SERS tags exhibit extremely high brightness in the SERS imaging due to the high SERS activity of GNS and encapsulation of a large number of NTP, which renders high sensitivity in the SERS sensing and imaging. Although previous work showed that silica exerts little in vivo cytotoxicity, the SERS tag is further modified with mPEG-silane to improve the biocompatibility. Extinction spectra showed that there is a 30 nm red-shift in LSPR of SERS tag compared with the prepared GNS (FIG. 1), attributed to the change in refractive index after silica coating. TEM image confirms the successful coating of GNS with a 3-4 nm silica layer (F 1B).

Formation of a Nanoplex

A nanoplex is generally defined as a SERS tag comprising additional elements such as one or more targeting agents, one or more therapeutic agents, and/or combinations thereof. Preferred therapeutic agents used in the present invention include PSMA binding agents such as urea based small molecules having high affinity and specificity to PSMA, PSMA targeted phosphoramidate and phosphonate, 7E11 monoclonal antibody, J591 monoclonal antibody, 3C6 monoclonal antibody, and radiotherapeutic elements including $^{177}$Lu and $^{90}$Y. The development of urea-based small molecule PSMA inhibitors was pioneered by Pomper and co-workers. These urea-based small molecules have high affinity and specificity to the PSMA over-expressed on the prostate cancer cells as demonstrated in PET, SPECT and fluorescence imaging modalities. To further advance their utilization for SERS imaging of live cells, the Glu-urea-Lys-linker-NHS was grafted onto the SERS tag surface through the amine coupling chemistry (FIG. 1A). The functional urea component can specifically recognize the zinc site in PSMA. FIG. 1C shows SERS spectra of SERS tags and nanoplexes modified with urea-based PSMA targeting moiety. Several intense SERS features that are characteristic of the NTP molecule were observed, such as bands at 727 cm$^{-1}$ (ascribed to wagging vibrations of C—H, C—S and C—C), 853 cm$^{-1}$ (wagging vibration of C—H), 1080 cm$^{-1}$ (stretching vibration of C—S), 1110 cm$^{-1}$ (bending vibration of C—H), 1340 cm$^{-1}$ (stretching vibration of N—O), and at 1573 cm$^{-1}$ (stretching vibration of phenyl ring).

Figure 3A:
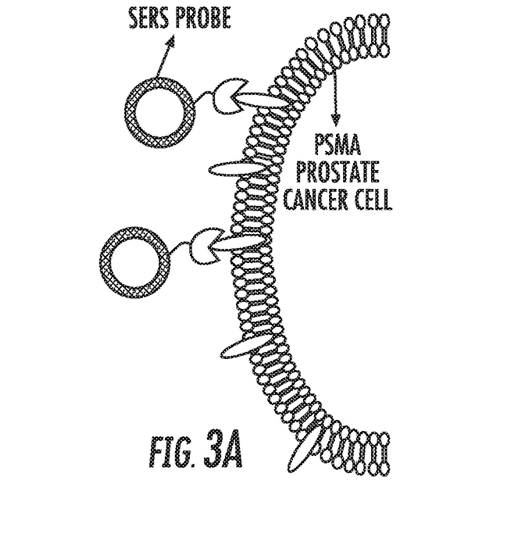
FIG. 3A-3C illustrates in vitro targeted cellular SERS imaging with the NTP-encoded nanoplex. (A) Schematic illustration of nanoplex targeted imaging of live cells. The nanoplex is prepared by modification of NTP-encoded SERS tag with the urea-based PSMA targeting moiety, N-{[(1S)-1-carboxy-3-methylbutyl)amino]carbonyl}-L-glutamic acid (ZJ43). (B) The urea-based small molecule has extremely high affinity toward the PSMA on the PC3-PIP cell surface. Bright-field images, Raman images and their overlaid images in the absence or presence of nanoplex (50 pM). (C) 785 nm near-infrared laser source (5 mW power and 1 s integration time/pixel) was used for the SERS imaging with 50×50 pixels over a 80 μm×80 μm area.

PSMA inhibitory activity of a nanoplex of the present invention was examined using a fluorescence-based PSMA inhibition assay according to a previously reported procedure [18]. The unmodified SERS tag and the urea-based small molecule PSMA inhibitor (N-{[(1S)-1-carboxy-3-methylbutyl]amino]carbonyl}-L-glutamic acid, ZJ43) were used for control (FIG. 3). We observed that this nanoplex exhibits extremely high affinity toward PC3-PIP cells with an IC$_{50}$ value of $2.0\times10^{-13}$ nM, nearly four orders of magnitude lower than the value ($1.6\times10^{-9}$ nM) of ZJ43 alone, analogs of which are currently used as clinical imaging agents to detect prostate cancer. Such remarkably high affinity suggests better long-term stability in SERS imaging, and also improved pharmacokinetics and prolonged contact time to the targeting sites leading to much improved treatment opportunities in cancer therapy. We conclude that the ultrahigh affinity is ascribed to the multiple targeting sites existing on a single SERS tag surface due to modification of multiple urea-based targeting ligands. Cells were seeded into 96-well plates containing incubation medium and incubated over various time intervals. We prefer the isogenic PC3-PIP vs PC3-Flu comparison as the two lines are phenotypically identical, differing only in PSMA expression [7]. The growth of cells was first evaluated in the absence or presence of SERS tag and nanoplex (FIG. 2A). PC3-PIP cells grow over the prolonged incubation time and follow the same growth trend in both absence and presence of SERS tag, but the cell growth reaches saturation after 6 days. In contrast, growth of PC3-PIP cells is dramatically slow in the presence of nanoplex, and the cell number even decreases slightly after 4-day incubation. This indicates the inhibitory growth of PC3-PIP cells by the nanoplex. To examine the selectivity and specificity in vitro, PSMA–PC3-Flu and breast cancer MDA-MB-231 cells were used for control. As can be seen from FIG. 2B, breast cancer MDA-MB-231 cell grows much faster in comparison with PSMA+ PC3-PIP and PSMA–PC3-Flu cells, while PC3-PIP cells have a lowest growth rate. This is consistent with the fact that breast cancer MDA-MB-231 cells grow faster than PC3-PIP and PC3-Flu cells under normal incubation conditions without addition of any SERS tag or nanoplex. It is worth noting that SERS tag and nanoplex have little effect on growth of both PC3-Flu and breast cancer MDA-MB-231 cells. Therefore, the present nanoplex will inhibit the growth of the PC3-PIP cell line but exert less cytotoxicity. These results indicate that the present nanoplex has excellent selectivity and specificity toward PSMA+PC3-PIP cells, which is ascribed to the targeting binding of functional urea-based small molecule onto the PSMA on the PC3-PIP cell surface.

Creating and Detecting Raman Signals

Figure 3B:
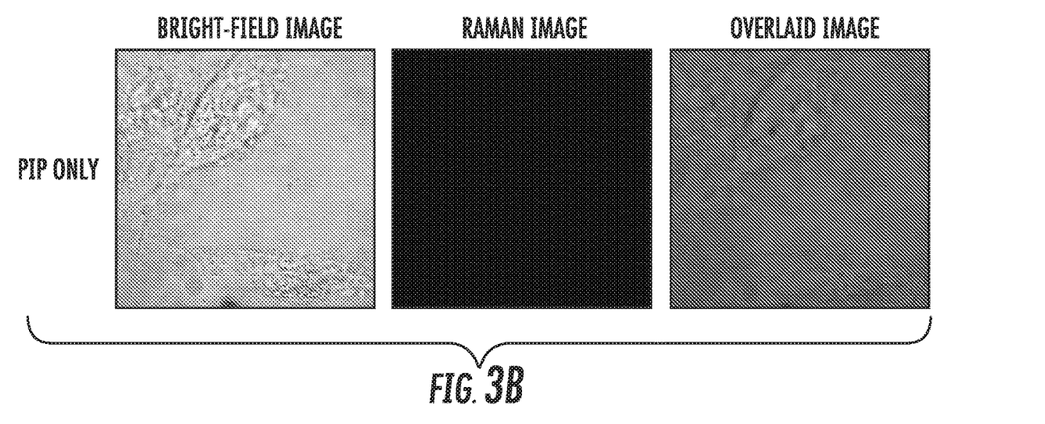
Figure 3C:
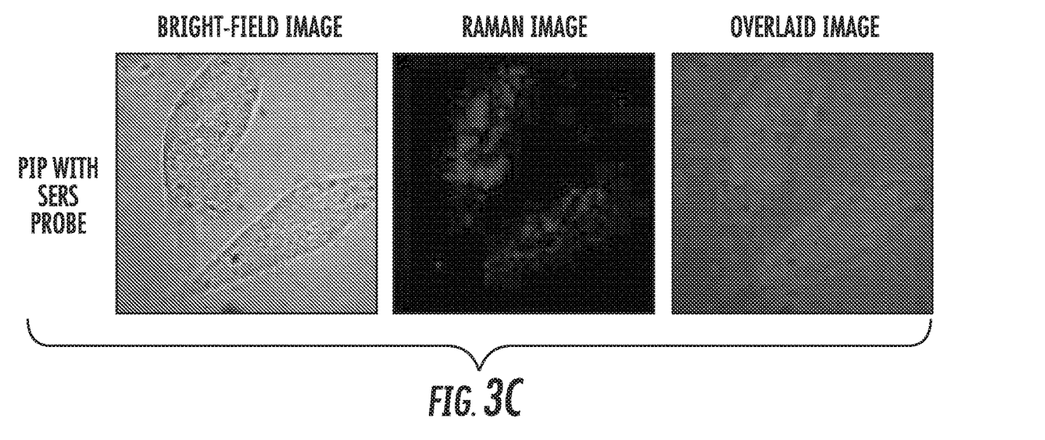

To evaluate the targeted imaging of live cells, we first performed proof-of-concept investigation of SERS imaging of PSMA+PC3-PIP cells in the absence or presence of nanoplexs (FIG. 3). FIG. 3A briefly shows the principle of operation of targeted cell imaging. The functional targeting ligands on the nanoplex can specifically recognize the PSMA over-expressed on the PC3-PIP cells. PSMA+PC3-PIP cells were placed onto a custom-built quartz-bottomed petri dish. The cells were allowed to adhere to the quartz-bottomed dish for at least 24 h before adding the nanoplex. After the nanoplexs were added into the PC3-PIP cells and incubated for 1 h, the incubation medium was replaced with freshly prepared incubation medium, and stood for 12 h. We obtained bright-field images and confocal Raman images. A laser beam (5 mW, 785 nm) was focused onto a single cell, and scanned the cells with 50×50 pixels over an 80 μm×80 μm area. There is no observable SERS signal existing in the absence of nanoplex, however, after PC3-PIP cells were incubated in 50 pM nanoplex, extremely enhanced SERS signatures from NTP in nanoplex can be observed. We constructed the SERS image of examined cells using the strong SERS signature of stretching vibration of N—O at 1340 cm$^{-1}$ after background subtraction (FIG. 3B,C). It is clear that live cells exhibit strong brightness and the SERS image shows the typical cell shape as can be seen in the overlaid image. Therefore, our developed nanoplex is able to perform the targeted imaging of live cells with significantly over-expressing PSMA on the PC3-PIP cells.

Figure 4A:
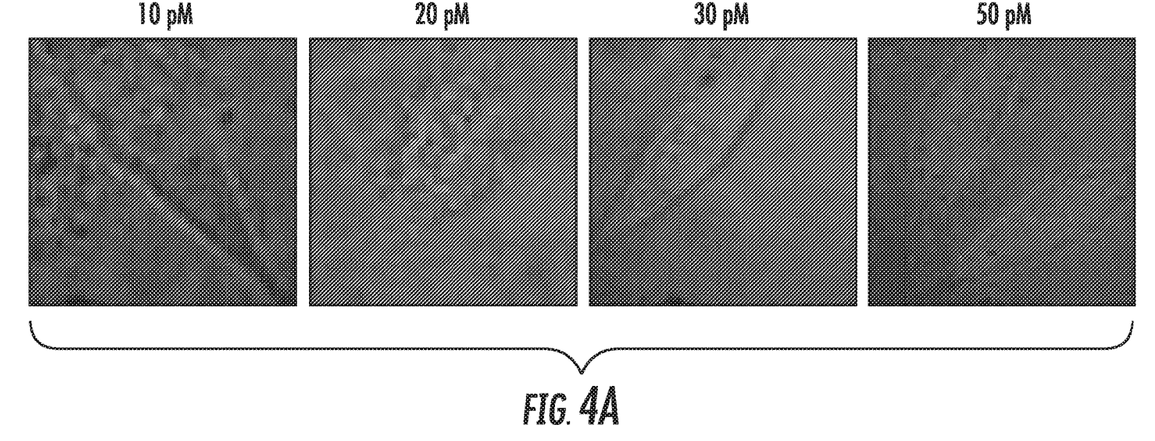
FIG. 4A-4B illustrates dose-dependent SERS images of (A) PSMA+PC3-PIP and (B) PSMA−PC3-Flu cells after incubation in various concentrations (10, 20, 30 and 50 pM) of nanoplex. SERS images were overlaid with bright-field images. The SERS intensity on a single PC3-PIP cell increases with the increasing nanoplex concentration while there is no significant change in SERS intensity observed in the case of PC3-Flu cell. The nanoplex first targets the PSMA over-expressed on the surface of PC3-PIP cells and enters the cell by the PSMA-assisted internalization. SERS measurements were performed with 785 nm laser, 5 mW power and 1 s integration time with 50×50 pixels over an 80 μm×80 μm area.
Figure 4B:
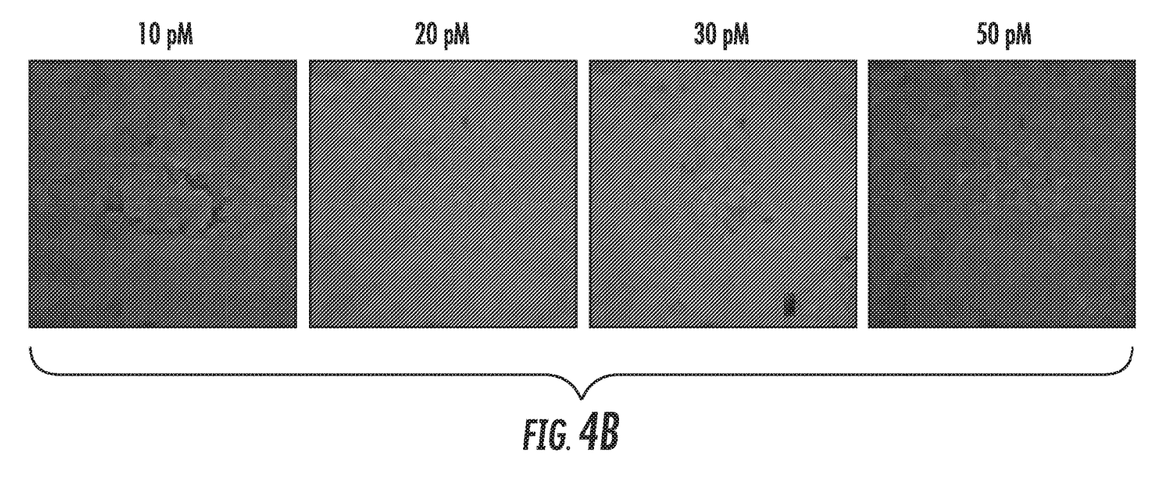

We further examined dose-dependent SERS imaging in both cases of PC3-PIP and PC3-Flu cells (FIG. 4). With increasing nanoplex concentration from 10 pM to 50 pM, the SERS intensity at the peak of 1340 cm$^{-1}$ increases for PSMA+PC3-PIP cells. The SERS intensity increases slightly for PSMA–PC3-Flu cells as the increasing nanoplex concentration, however, there is not significant aggregation of nanoplex within cells. The increased SERS intensity in PSMA–PC3-Flu cells is due to the internalization of nanoplex. We determined the average SERS intensity on a single cell by considering the SERS intensity over the total pixel number on a single cell (Figure S4). The SERS intensity increases as the increasing concentration of nanoplex for PC3-PIP cells while there is less increase observed for PC3-Flu cells. It is worth noting that the nanoplex first appears around the cell in the relative low concentration (10 pM and 20 pM), and then within the cell when the nanoplex reaches much higher concentrations, for example, 30 pM and 50 pM, in PC3-PIP cells. This indicates that the nanoplex can enter the PC3-PIP cell after targeting the PSMA on the cell surface, which may be attributed to the internalization of nanoplex into the cell. This is actually consistent with the previous observation that the PSMA can assist the internalization process. We further confirmed the internalization of nanoplex used in present work by TEM (FIG. 6). As more nanoplexes target onto the PSMA on the PC3-PIP cell surface at high concentrations, the internalization of nanoplex is capable of enhancing SERS intensity and improving the imaging sensitivity.

In Vitro Applications

The nanoplex of the present invention represents the first Raman probe for cell recognition and associated diagnosis in prostate cancer and includes a SERS tag design and fabrication of gold (Au) nanostar-derived SERS attached to a targeting agent that afford unprecedented sensitivity beyond those produced from standard plasmonic nanoparticles due to the lightning rod effect at the sharp tips. By independently tailoring the geometry of the nanostar core and protrusions, we have shown the flexibility to tune the resonance enhancement to the "tissue-transparent" near infrared window thus enabling even deeper imaging. This detection method itself would add significant value in identifying tumor margins during prostatectomy. In vivo applications would preferably use an endoscopic laser to excite a nanoplex that had been administered to a patient and another endocscope, able to detect the image of the nanoplex and/or the image of the cell, tissue, or organ. The endoscope would be connected to a computer and the image would appear on the attached computer screen. Another embodiment of the present invention is the formation of nanoplex comprising a targeting agent, preferably a PSMA-targeted agent, and a therapeutic moiety, preferably $^{177}$Lu. The unusually high affinity of the PSMA-targeted nanoplex—higher affinity than any species reported for targeting PSMA—makes it ideal for molecular radiotherapy, which requires a high-affinity interaction for long residence times of the therapeutic with tumor. This approach is further transformative as it allows one to visualize in real-time the distribution and action of the therapeutic agents in in vivo by transducing the presence of PSMA at the tissue level to characteristic Raman spectral patterns (that is unaffected by the tissue autofluorescence levels).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Chemicals and Materials.

Chloroauric acid (HAuCl$_4$·xH$_2$O, 99.999% trace metals basis), trisodium citrate dihydrate (HOC(COONa)(CH$_2$COONa)$_2$·2H$_2$O, ≥99%), poly(vinylpyrrolidone) (PVP, (C$_6$H$_9$NO)$_n$, molecular weight-10 kg/mol), sodium borohydride (≥99%), N,N-dimethyformamide (DMF, anhydrous 99.8%), dimethyl sulfoxide (DMSO, 99.5%, molecular biology), sodium hydroxide (pellets, 99.99% trace metals basis), (3-aminopropyl) trimethoxysilane (APTMS, 97%), sodium silicate (Na$_2$O(SiO$_2$)$_x$·xH$_2$O, reagent grade), 4-nitrothiophenol (NTP, technical grade 80%) and sodium hydroxide (NaOH, 99.99%), RPMI 1640, fetal bovine serum (FBS), Penicillin-Streptomycin, WST-1 reagent were purchased from Sigma-Aldrich (St. Louis, MO). Methoxy-poly(ethylene glycol)-silane (mPEG-silane, molecular weight-2 kg/mol) was obtained from Laysan Bio (Arab, AL). Phosphate buffered saline (1×PBS, pH 7.4) solution was purchased from Quality Biology (Gaithersburg, MD). PYREX® Petri Dish was purchased from Corning Incorporated (Corning, NY), and quartz coverslip from Alfa Aesar (Ward Hill, MA). All other reagents or solvents used in this study were of analytical grade and used without further purification.

Synthesis of SERS Tags and its Conjugates.

Synthesis of SERS tags. NTP-encoded SERS tags were synthesized according to a previously reported procedure by our group. Gold nanostars (GNSs) were first synthesized by the seed-mediated growth method detailed in our previous work [29]. Briefly, to prepare the gold seed solution, 1 mL of 1 wt % HAuCl$_4$·xH$_2$O aqueous solution was diluted to 90 mL with deionized water followed by the addition of 2 mL 38.8 mM trisodium citrate aqueous solution. 1 mL of freshly prepared NaBH$_4$ solution (0.075 wt % in 38.8 mM trisodium citrate aqueous solution) was then slowly added. After the reaction was kept at room temperature overnight, 50 mL of the gold seed solution was mixed with PVP (10 mM) at room temperature and kept stirring for 24 h to obtain the PVP-coated gold seed solution. After that, 82 µL of 50 mM HAuCl$_4$·xH$_2$O aqueous solution was added to 15 mL DMF of 10 mM PVP, and then 86 µL of PVP-coated gold seed solution was rapidly added with constant stirring at room temperature for 3 h. The extinction spectrum becomes unchanged as the growth is beyond 30 min, indicating that the growth of GNS is completed within 30 min. The resulting GNS nanoparticles were successively centrifuged at 11000 rpm for 15 min and washed at least three times with ethanol, and re-suspended into 15 mL deionized water for preparation of SERS tags. To prepare the SERS tag, a freshly prepared solution of NTP (10 µM) was added dropwise to the GNS colloids prepared above under continuous magnetic stirring. After 30 min, 10 µL of freshly prepared 50 mM APTMS ethanolic solution was added and kept stirring for another 30 min. The pH value of reaction solution was adjusted to around 9-10 by addition of NaOH aqueous solution. Following this, 200 µL of freshly prepared 0.54 wt % trisodium silicate solution was added slowly, and then stirred for one day. 5 mL anhydrous ethanol was subsequently added to generate a condensed silica layer. The reaction solution was kept standing for one more day, then centrifuged and washed with anhydrous ethanol and deionized water, respectively. The pellets were re-dispersed into 1×PBS for further use.

Synthesis of Urea-SERS Tag Conjugates.

The prepared SERS tags were conjugated with a low molecular weight, urea-based PSMA-targeting moiety, Glu-urea-Lys-linker-NHS, previously developed in the Pomper group [7]. To improve the biocompatibility, SERS tags were first co-modified by mPEG-silane and APTMS with a 1:2 molar ratio. Typically, 5.65 µM mPEG-silane and 11.3 µM APTMS were added to 50 pM SERS tag ethanolic solution. After the reaction continued for 12 h with magnetic stirring, the solution was centrifuged and washed with ethanol and deionized water, respectively. The resulting solids were re-dispersed into 1×PBS followed by dropwise addition of Glu-urea-Lys-linker-NHS (10% v/v) in DMSO within 30 min under a shaking rate of 60 rpm. After that, the solution was shaken at 60 rpm for 2 h. The reaction solution was washed at least 4 times with 1×PBS (4° C.) to remove excess unbound Glu-urea-Lys-linker-NHS, and the pellets from the final wash were the conjugates called nanoplexes, and re-dispersed into 1 mL 1×PBS.

Cell Culture.

Human prostate cancer PC3 cells with over-expressing PSMA (PC3-PIP) or negatively-expressing PSMA (PC3-Flu) were obtained from Dr. Warren Heston (Cleveland Clinic, Cleveland, OH). Both PSMA+PC3-PIP and PSMA−PC3-Flu cell lines were incubated in RPMI 1640 supplemented with 10% FBS and 1% Penicillin-Streptomycin in a humidified incubator at 37° C./5% $CO_2$.

For SERS imaging of live cells, the cells ($1 \times 10^6$ cells/mL) were seeded in a 60 mm quartz-bottomed petri dish, and then allowed to adhere to the quartz-bottomed dish overnight. Nanoplexes of various concentrations (10, 20, 30 and 50 pM) were added to the petri dish, and incubated for 1 h followed by replacement of incubation medium with freshly prepared RPMI 1640 incubation medium and standing for 12 h before SERS imaging was implemented.

In Vitro Cellular Cytotoxicity Test.

The cytotoxicity of the nanoplex was evaluated by a WST-1 assay. Cells ($1 \times 10^4$ cells/well) were seeded onto 96-well plates and incubated for 24 h in RPMI 1640 supplemented with 10% FBS and 1% Penicillin-Streptomycin. Then, 50 pM nanoplexes were added, and after incubation for a preset time, the WST-1 reagent (4-[3-(4-Iodophenyl)-2-(4-nitrophenyl)-2H-5-tetrazolio]-1,3-benzene disulfonate) was added into the corresponding wells and incubated for 1 h in the 37° C./5% $CO_2$ incubator before the absorbance was measured.

SERS Measurements.

All SERS measurements were performed using a home-built, inverted high-speed confocal Raman microscope in our laboratory. A compact LM series solid laser of 785 nm emission wavelength (Ondax) filtered with a clean-up filter (LL01-785-12.5, Semrock) was used as the excitation source and re-directed to the dual-axes galvanometer mirrors (GVS112, Thorlabs). High-speed XY scanning was performed by the galvanometer mirrors. A 0.65-1.25 NA, 60× oil immersion objective lens (RMS60X-PFOD, Olympus) was used to focus the laser light to and collect the Raman-scattering light from the sample. The backscattered light was collected by a 50 µm multimode fiber (M14L01, Thorlabs), delivered to an HoloSpec f/1.8 spectrograph (Kaiser Optical Systems, Andor) and the dispersed light was finally detected by an iDus CCD Camera (DU420A-BEX2-DD, Andor). LabView 2013 (National Instruments) and MATLAB 2013 (Mathworks) were used to control the system, acquire the data, and analyze the data. Raman and SERS spectra were recorded using 5 mW laser power and 1 s integration time.

Characterization.

Extinction spectra for the GNS and SERS tags were recorded on a Shimadzu UV-2401 spectrometer. Transmission electron micrographs (TEMs) were acquired using the FEI Tecnai G2 Spirit TWIN transmission electron microscope at an accelerating voltage of 120 kV. The samples for TEM were prepared by deposition of a drop of the suspensions in ethanol onto ultrathin Formvar-coated 200 mesh copper grids (Ted Pella, Inc.) and left to dry in air. Cell samples for TEM imaging were prepared according to the procedure reported in the literature [30] after incubation as described above. Briefly, after incubation with nanoplexes, cells were fixed in a 0.1 M sodium cacodylate buffer solution (pH 7.4) containing 3.0% formaldehyde, 1.5% glutaraldehyde, 5.0 mM $CaCl_2$ and 2.5% sucrose for 1 h, rinsed with 0.1 M sodium cacodylate buffer solution (pH 7.4) of 2.5% sucrose, and then post-fixed for 1 h in Palade's buffered solution of 1% osmium tetroxide. After dehydration with graded series of cold ethanol (70, 90 and 100%), the samples were washed three times with fresh 100% ethanol, and then twice with propylene oxide at room temperature before being transferred to fresh 100% Epon and embedded in fresh 100% Epon under vacuum for 4-6 h. After kept at 60° C. for 24-48 h, serial sections were cut and mounted onto copper-grids for TEM examination.

REFERENCES

7. Banerjee, S. R.; Pullambhatla, M.; Byun, Y.; Nimmagadda, S.; Foss, C. A.; Green, G.; Fox, J. J.; Lupold, S. E.; Mease, R. C.; Pomper, M. G. Sequential SPECT and Optical Imaging of Experimental Models of Prostate Cancer with a Dual Modality Inhibitor of the Prostate-Specific Membrane Antigen. *Angew. Chem. Int. Ed.* 2011, 50, 9167-9170.

18. Chen, Y.; Foss, C. A.; Byun, Y.; Nimmagadda, S.; Pullambhatla, M.; Fox, J. J.; Castanares, M.; Lupold, S. E.; Babich, J. W.; Mease R. C.; Pomper, M. G. Radiohalogenated prostate-specific membrane antigen (PSMA)-based ureas as imaging agents for prostate cancer. *J. Med. Chem.* 2008, 51, 7933-7943.

with plasmon-enhanced Raman spectro-immunoassay. *Chem. Sci.* 2015, 6, 3906-3914.

29. Li, M.; Kang, J. W.; Dasari, R. R.; Barman, I. Shedding Light on the Extinction-Enhancement Duality in Gold Nanostar-Enhanced Raman Spectroscopy. *Angew. Chem. Int. Ed.* 2014, 53, 14115-14119.

30. Perkins, E.; McCaffery, J. M. Conventional and Immunoelectron Microscopy of Mitochondria (Eds.: Leister, D. and Herrmann J. M.), Humana Press (Tomowa, NJ), 2007, Constitutive and Antibody-induced Internalization of Prostate-specific Membrane Antigen. *Cancer Res.* 1998, 58, 4055-4060.

The invention claimed is:

1. A Surface-Enhanced Raman Spectroscopy (SERS) reporter nanoplex comprising a compound of the formula:

wherein:
  L is a linker; and
  Ⓢ is a SERS tag;
wherein the SERS tag comprises at least one Raman reporter molecule disposed between a gold nanostar and a silica layer on its surface, wherein the at least one Raman reporter molecule is selected from 4-nitrothiophenol (NTP), 4-mercaptobenzoic acid (MBA), malachite green isothiocyanate (MGITC), and rhodamine B isothiocyanate (RBITC).

2. The SERS reporter nanoplex of claim 1, wherein the SERS tag is modified with a methoxy-poly(ethylene glycol) (mPEG)-silane moiety.

3. The SERS reporter nanoplex of claim 1, further comprising a radiotherapeutic element.

4. The SERS reporter nanoplex of claim 3, wherein the radiotherapeutic element is $^{177}$Lu or $^{90}$Y.

5. The SERS reporter nanoplex of claim 1, comprising a compound of the formula:

wherein:
  mPEG is a methoxy-poly(ethylene glycol)-silane moiety.

6. A method of imaging a cell, tissue, and/or organ using a Raman spectroscopy reporter, the method comprising:
  a) providing a SERS nanoplex of claim 1;
  b) applying the SERS nanoplex to the the cell, tissue, and/or organ so that the nanoplex binds to the cell, tissue, and/or organ;
  c) exciting the SERS nanoplex with an energy source to create a Raman signal;
  d) detecting the Raman signal; and
  e) constructing an image from the Raman signal.

7. The method of claim 6 wherein the nanoplex binds to a prostate cancer cell.

8. The method of claim 6, wherein the nanoplex binds to an in vitro cell, tissue, and/or organ.

9. The method of claim 6, wherein the nanoplex binds to an in vivo cell, tissue, and/or organ.

10. The method of claim 9, wherein the energy source is an endoscopic laser.

11. The method of claim 10, wherein the endoscopic laser emits light in a range of 700 nm to 1000 nm.

12. The method of claim 11, wherein the Raman signal is detected by an endoscopic light detector that is connected to a computer.

13. The method of claim 12, wherein the computer is attached to a screen that displays the image.

14. A method of determining a location of a therapeutic agent on a cell, tissue, and/or organ, the method comprising:
  a) providing a SERS nanoplex of claim 1;
  b) applying the nanoplex to a cell, tissue, and/or organ so that the nanoplex binds to the cell, tissue, and/or organ;
  c) exciting the nanoplex with an energy source to create a Raman signal;
  d) detecting the Raman signal; and
  e) constructing an image from the Raman signal to determine the location of the therapeutic agent on the cell, tissue, and/or organ, wherein the therapeutic agent is selected from an ester-urea based and Glu-urea-Lys-linker based PSMA binding agent, PSMA targeted phosphoramidate and phosphonate, 7E11 monoclonal antibody, J591 monoclonal antibody, 3C6 monoclonal antibody, $^{177}$Lu, and $^{90}$Y.

15. The method of claim 14, wherein the cell, tissue, and/or organ is a prostate cancer cell.

16. The method of claim 14, wherein the nanoplex binds to in vitro cell, tissue, and/or organ.

17. The method of claim 14, wherein the nanoplex binds to in vivo cell, tissue, and/or organ.

18. The method of claim 17, wherein the energy source is an endoscopic laser.

19. The method of claim 18, wherein the endoscopic laser emits light in a range of 700 nm to 1000 nm.

20. The method of claim 19, wherein the Raman signal is detected by an endoscopic light detector that is connected to a computer.

21. The method of claim 20, wherein the computer is attached to a screen that displays the image of the location of the therapeutic agent.

* * * * *